(12) United States Patent
Durr et al.

(10) Patent No.: US 12,361,097 B2
(45) Date of Patent: *Jul. 15, 2025

(54) DEEP LEARNING BASED IMAGE ENHANCEMENT

(71) Applicant: The Johns Hopkins University, Baltimore, MD (US)

(72) Inventors: Nicholas J. Durr, Baltimore, MD (US); Taylor L. Bobrow, Chesapeake, VA (US); Faisal Mahmood, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/632,463

(22) Filed: Apr. 11, 2024

(65) Prior Publication Data

US 2024/0281500 A1     Aug. 22, 2024

Related U.S. Application Data

(63) Continuation of application No. 17/309,100, filed as application No. PCT/US2019/057450 on Oct. 22, 2019, now Pat. No. 11,971,960.

(Continued)

(51) Int. Cl.
*G06F 18/24* (2023.01)
*G06N 3/045* (2023.01)
(Continued)

(52) U.S. Cl.
CPC ............ *G06F 18/24* (2023.01); *G06N 3/045* (2023.01); *G06N 3/088* (2013.01); *G16H 30/20* (2018.01)

(58) Field of Classification Search
CPC .. A61B 1/000095; G06F 18/24; G06N 3/045; G06N 3/08; G06N 3/088; G16H 30/20; G06V 20/69
See application file for complete search history.

(56) References Cited

U.S. PATENT DOCUMENTS

2003/0019933 A1*   1/2003   Tsikos ..................... G06K 7/10
                                                                  235/454
2012/0235885 A1*   9/2012   Miller .................... G06Q 30/02
                                                                   345/8

(Continued)

FOREIGN PATENT DOCUMENTS

| CN | 108430306 A | 8/2018 |
|---|---|---|
| WO | 2014145246 A1 | 9/2014 |
| WO | 2018143180 A1 | 8/2018 |

OTHER PUBLICATIONS

Yuhui Ma, "Speckle noise reduction in optical coherence tomography images based on edge-sensitive cGAN, "Oct. 2, 2018, vol. 9, No. 11 | Nov. 1, 2018, Biomedical Optics Express 5129,pp. 1-16.*

(Continued)

*Primary Examiner* — Omar S Ismail
(74) *Attorney, Agent, or Firm* — Harrity & Harrity, LLP

(57) ABSTRACT

A device may receive a coherent energy illuminated image, of a particular object, that includes laser speckle. The device may process, using a laser speckle reduction model, the coherent energy illuminated image to generate a laser speckle-reduced image. The device may provide the laser speckle-reduced image as output to permit diagnostics based on the laser speckle-reduced image.

20 Claims, 8 Drawing Sheets

Related U.S. Application Data

(60) Provisional application No. 62/749,242, filed on Oct. 23, 2018.

(51) Int. Cl.
  *G06N 3/088* (2023.01)
  *G16H 30/20* (2018.01)

(56) References Cited

U.S. PATENT DOCUMENTS

| | | | | |
|---|---|---|---|---|
| 2013/0258091 | A1* | 10/2013 | Ozcan | G01N 15/1433 348/79 |
| 2014/0285650 | A1* | 9/2014 | Ishiwata | G02B 21/16 382/133 |
| 2014/0288373 | A1* | 9/2014 | Henley | A61B 1/01 600/182 |
| 2015/0051498 | A1* | 2/2015 | Darty | G01J 3/2803 600/407 |
| 2015/0248770 | A1* | 9/2015 | Hasegawa | G06T 7/12 382/131 |
| 2016/0341951 | A1* | 11/2016 | Tearney | A61B 1/00096 |
| 2017/0019575 | A1* | 1/2017 | Dhadwal | G02B 23/2484 |
| 2017/0173262 | A1* | 6/2017 | Veltz | G16H 20/17 |
| 2017/0245747 | A1* | 8/2017 | Soudagar | G02B 6/4298 |
| 2018/0220589 | A1* | 8/2018 | Burden | A01G 3/085 |
| 2018/0293739 | A1* | 10/2018 | Gupta | G06V 10/62 |
| 2019/0005351 | A1* | 1/2019 | Zhou | G01N 15/1459 |
| 2019/0293620 | A1* | 9/2019 | Farkas | G01N 21/3563 |
| 2020/0041261 | A1* | 2/2020 | Bernstein | A61B 90/37 |
| 2020/0394791 | A1* | 12/2020 | Pang | G06N 3/045 |
| 2022/0019861 | A1 | 1/2022 | Durr et al. | |

OTHER PUBLICATIONS

Harry M. Salinas, "Comparison of PDE-Based Nonlinear Diffusion Approaches for Image Enhancement and Denoising in Optical Coherence Tomography,"Oct. 13, 2006, IEEE Transactions On Medical Imaging, vol. 26, No. 06, Jun. 2007, pp. 761-769.*

Yunzhe Li, "Deep speckle correlation: a deep learning approach toward scalable imaging through scattering media,"Sep. 25, 2018, vol. 5, No. 10 / Oct. 2018 / Optica, pp. 1181-1188.*

Ming Chen, "Laser speckle contrast imaging of blood flow in the deep brain using microendoscopy,"Nov. 14, 2018,vol. 43, No. 22 / Nov. 15, 2018 / Optics Letters, pp. 5627-5629.*

Mohammad R. N. Avanaki, "Speckle reduction using an artificial neural network algorithm,"Jul. 11, 2013,Article in Applied Optics • Jul. 2013,vol. 52, Issue 21,pp. 5050-5053.*

Orly Liba et al.,"Speckle-modulating optical coherence tomography in living mice and humans," Jun. 20, 2017, Nature Communications, 8:15845 | DOI: 10.1038/ncomms15845,pp. 1-9.*

Avanaki M.R.N., et al., "Speckle Reduction using an Artificial Neural Network Algorithm," Article in Applied Optics, Jul. 2013, vol. 52(21), pp. 5050-5053.

Chen M., et al., "Laser Speckle Contrast Imaging of Blood flow in the Deep Brain using Microendoscopy," Optics Letters, Nov. 2018, vol. 43(22/15), pp. 5627-5629.

International Search Report and Written Opinion for Application No. PCT/US2019/057450, mailed on Jan. 20, 2020, 6 pages.

Li Y., et al., "Deep Speckle Correlation: A deep Learning Approach toward Scalable Imaging through Scattering Media," Optica, Sep. 2018, vol. 5(10), pp. 1181-1188.

Salinas H.M., et al., "Comparison of PDE-Based Nonlinear Diffusion Approaches for Image Enhancement and Denoising in Optical Coherence Tomography," IEEE Transactions on Medical Imaging, Oct. 2006, vol. 26(6), pp. 761-769.

Yuhui M.A., et al., "Speckle Noise reduction in Optical Coherence Tomography Images based on Edge-sensitive cGAN," Biomedical Optics Express, Oct. 2018, vol. 9(11), pp. 1-16.

* cited by examiner

DEEP LEARNING BASED IMAGE ENHANCEMENT

RELATED APPLICATION

This application is a continuation of U.S. patent application Ser. No. 17/309,100, filed Apr. 23, 2021 (now U.S. Pat. No. 11,971,960), which is a 371 national stage of PCT Application PCT/US2019/057450, filed on Oct. 22, 2019, which claims priority to U.S. Provisional Patent Application No. 62/749,242, filed on Oct. 23, 2018, the contents of each of which are hereby expressly incorporated by reference herein.

GOVERNMENT LICENSE RIGHTS

This invention was made with U.S. Government support under grant R21 EB024700, awarded by the National Institute of Health. The U.S. Government has certain rights in the invention.

BACKGROUND

Imaging devices, such as cameras, video cameras, and/or the like, may be used to capture images. For example, in endoscopy, an incoherent light source may be disposed at a proximal end of an endoscope, with illumination being provided via a fiber bundle from a distal end of the endoscope to illuminate an object (e.g., intestinal tissue), and an imaging device may be disposed at the distal end of the endoscope to capture an image of the object under incoherent illumination from the incoherent light source. The imaging device may provide an image to a client device. The client device may provide the image for display to enable a diagnostician to perform a diagnosis of a medical condition based on the image.

DETAILED DESCRIPTION

Figure 1A:
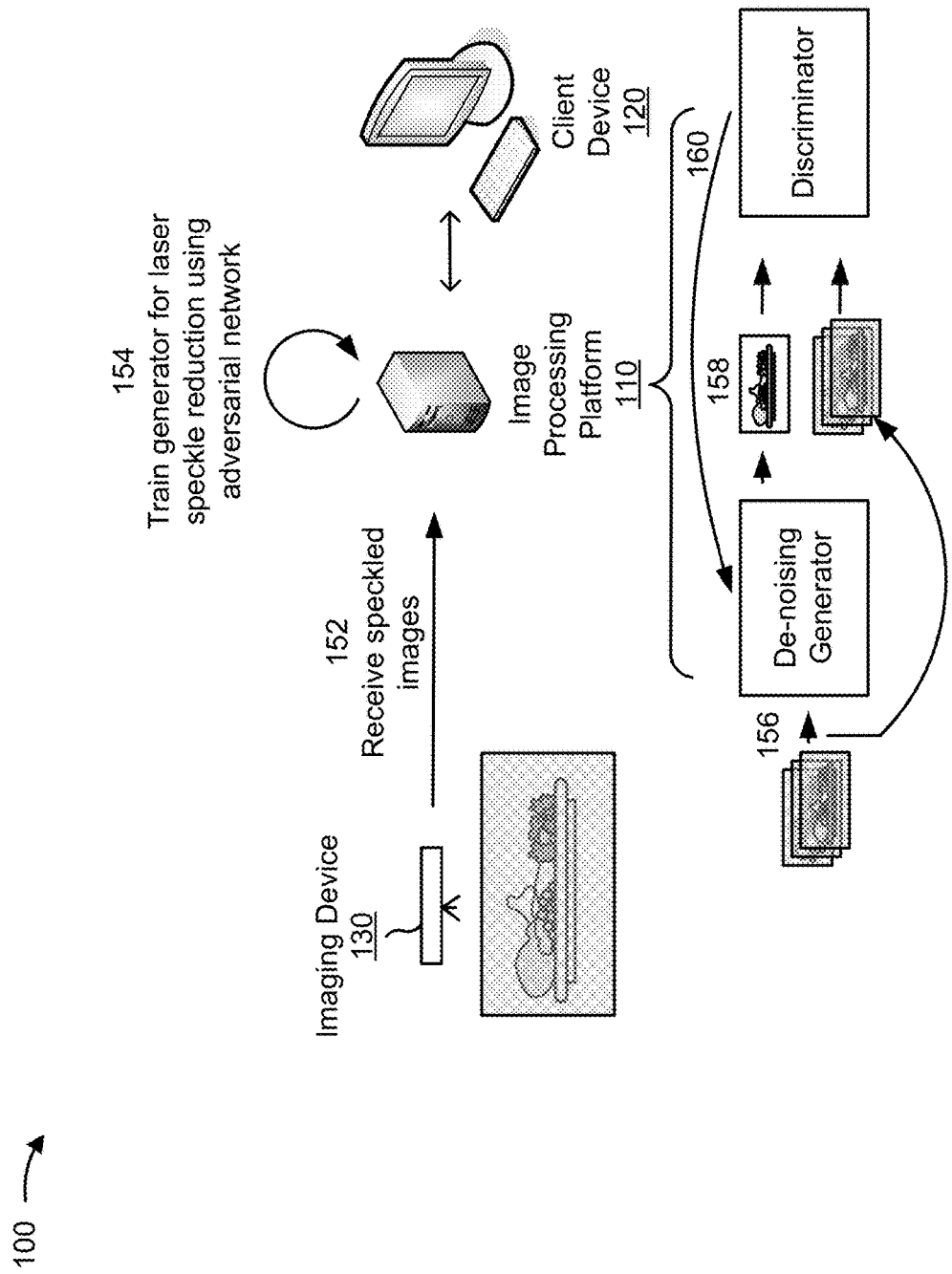
FIGS. 1A and 1B are diagrams of an example implementation described herein.

The following detailed description of example implementations refers to the accompanying drawings. The same reference numbers in different drawings may identify the same or similar elements.

As described above, a diagnostician may diagnose a medical condition based on an image captured of an object. The image may be illuminated under incoherent illumination by a light source, which may enable an imaging device to capture the image. However, a light source providing incoherent energy for illumination may be excessively large, may require an excessively large optical fiber, may give off excessive amounts of heat, may be associated with poor life span, and/or may be associated with excessive cost. Thus, a laser diode may be used to provide coherent energy for illumination of an object for imaging. For example, the laser diode may be optically coupled to a relatively small optical fiber, in a relatively efficient manner to direct coherent energy illumination to the object to enable imaging. Using coherent energy for illumination may enable relatively small etendue, improved bandwidth selectivity of the illumination, reduced cost, improved on/off selectivity (e.g., reduced time to pulse the illumination), reduced heat dissipation, and/or the like, thereby improving imaging.

Some images may be subject to conditions that result in a poor quality image. For example, imaging under coherent energy illumination may be subject to noise (e.g., laser speckling), as a result of constructive and destructive interference between wavefronts emitted by the laser diode. One technique to reduce laser speckle is to widen a bandwidth of a laser providing coherent energy illumination; however, this may negate advantages of using coherent energy (e.g., by causing increased etendue, reduced bandwidth selectivity, and/or the like). Alternatively, optical fibers may be mechanically vibrated to reduce temporal coherence of coherent energy illumination, thereby randomizing laser speckle; however, such a technique may be inappropriate for increasingly miniaturized applications or high-speed imaging. Alternatively, a diffuser may be used to vary a wavefront phase during image integration (i.e., during a period of time for image capture by an imaging device), thereby randomizing laser speckle and enabling time-averaging of laser speckle, which may reduce an impact of laser speckle. However, for that approach to be effective, image integration time may need to be greater than a threshold, which may prevent use of coherent energy illumination in high-speed applications, such as real-time or near real-time imaging. As another example of a condition under which a poor quality image may be obtained, imaging under dim illumination or overly bright illumination. Similarly, parameters of an imaging device may result in a poor quality image, such as exposure time, frame rate, resolution, and/or the like.

Some implementations described herein may enable image enhancement for imaging using a deep learning technique. For example, an image processing platform may receive a coherent energy illuminated image, and may use a generative adversarial networks (GANs) trained neural network to alter the coherent energy illuminated image to generate a new image with reduced laser speckle. In this way, the image processing platform may enable use of coherent energy illumination, thereby improving imaging relative to using incoherent energy illumination as described above, while enabling use at high speeds by avoiding a need for coherence reduction or laser speckle randomization. Additionally, or alternatively, the image processing platform may use the GANs trained neural network to alter images captured under dim illumination, thereby enabling imaging under low-light conditions, such as during surgery. Additionally, or alternatively, the image processing platform may alter images captured with other flaws that reduce usability, such as by altering images with excessively bright illumination, poorly selected exposure time or frame rate, low resolution, and/or the like. In this way, the image processing platform may improve imaging, such as for medical diagnostics, for product inspection, for quality control, and/or the like.

Although some implementations described herein are described in terms of laser speckle reduction, implementations described herein may be used for other imaging modalities, such as for reducing noise in optical coherence tomography (OCT), ultrasound, and/or the like.

Figure 1B:
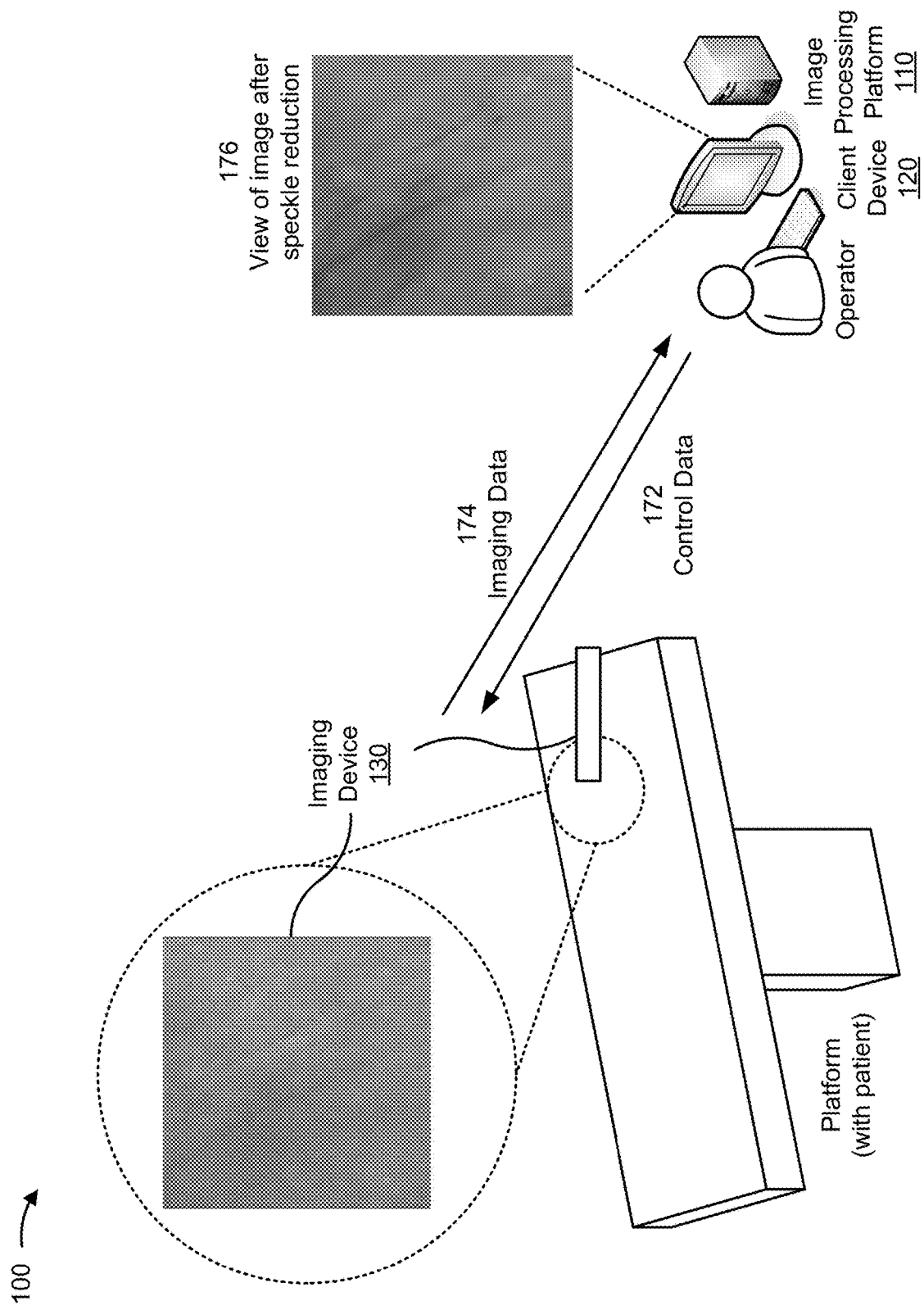

FIGS. 1A and 1B are diagrams of an example implementation 100 described herein. As shown in FIG. 1A, example implementation 100 includes an image processing platform 110, a client device 120, and an imaging device 130. In some implementations, image processing platform 110 may be implemented in a cloud computing environment, as described in more detail herein.

As further shown in FIG. 1A, and by reference number 152, image processing platform 110 and/or client device 120 may receive imaging from imaging device 130. For example, image processing platform 110 may receive images subject to a laser speckle condition, as described in more detail herein. In some implementations, image processing platform 110 may receive a threshold amount of imaging. For example, image processing platform 110 may receive a data set of imaging (e.g., hundreds, thousands, millions, or billions of images) and may divide the data set of images into a training set and a validation set for training a laser speckle reduction model.

In some implementations, image processing platform 110 may receive a set of image pairs of a set of training objects. In some implementations, a training object may be a medical object. For example, image processing platform 110 may receive a set of image pairs of images of intestinal tissue, muscle tissue, fatty tissue, and/or the like. In some implementations, the set of image pairs may be of a single type of object (e.g., human intestinal tissue). In some implementations, the set of image pairs may be of multiple types of training objects (e.g., human intestinal tissue, animal muscle tissue, and inorganic material).

In some implementations, the set of image pairs may be matched images. For example, during a training procedure, imaging device 130 may capture a first image of a training object under coherent energy illumination (e.g., with laser speckle) and a second image of the same training object under incoherent energy illumination (e.g., without laser speckle), thereby enabling training of the laser speckle reduction model, as described in more detail herein. In some implementations, the set of image pairs may be captured using multiple different imaging devices 130, thereby improving training of a laser speckle reduction model to reduce laser speckle for many different imaging devices 130. Additionally, or alternatively, imaging device 130 may obtain training imaging under other conditions, such as training imaging captured under dim conditions, excessively bright conditions, poorly selected frame rate or exposure conditions, low resolution conditions, and/or the like to train a model to perform image enhancement.

In some implementations, image processing platform 110 may segment the set of image pairs. For example, image processing platform 110 may divide a first image into a group of n image segments and a second image paired to the first image into a corresponding group of n image segments. In this case, image processing platform 110 may compare corresponding image segments (e.g., a first image segment with laser speckle and a second image segment without laser speckle, with different laser speckle, and/or the like), as described herein, thereby enabling training of the laser speckle reduction model to remove laser speckle. In this way, based on using image segments rather than whole images, image processing platform 110 may train the laser speckle reduction model to remove laser speckle rather than to perform some other action relating to a content of an image.

As further shown in FIG. 1A, and by reference number 154 image processing platform 110 may train a laser speckle reduction model, which may include training a generator using a generative adversarial networks (GANs) technique, such as a conditional GAN (cGANs) technique, an evolutionary GAN (eGANs), and/or the like. Although some aspects are described in terms of training a laser speckle reduction model, other types of models are possible to enhance images subject to other conditions as described herein.

In some implementations, image processing platform 110 may train a laser speckle reduction model based on the imaging.

In some implementations, to train a laser speckle reduction model, image processing platform 110 may train a generator model (which may be termed a generator network) and a discriminator model (which may be termed a discriminator network) using a GANs (e.g., a cGANs) neural network technique. For example, image processing platform 110 may use the generator model to generate a candidate image (e.g., with reduced laser speckle) based on a coherent energy illuminated image and based on an incoherent energy illuminated image (e.g., an image pair), as shown by reference numbers 156 and 158. In some implementations, image processing platform may use the discriminator network to evaluate a buffer of images relative to the candidate image. In this case, image processing platform 110 may use the discriminator model to evaluate whether the candidate image is associated with reduced laser speckle relative to the coherent energy illuminated image. Further, image processing platform 110 may use the discriminator model to provide feedback to the generator model, to enable training of the generator model, as shown by reference number 160. In this case, the generator model and the discriminator model are trained concurrently using a set of image pairs (e.g., which may be divided into training data and validation data), resulting in the generator model being trained to accurately generate laser speckle-reduced images based on coherent energy illuminated images, such that the laser speckle-reduced images better reflect a true image (e.g., what might be obtained using incoherent energy illumination) without introducing distortion or artifacts.

In some implementations, image processing platform 110 may avoid mode collapse associated with multiple sub-distributions of data within a particular distribution of data by using spectral normalization when training the models. In some implementations, image processing platform 110 may determine that the laser speckle reduction model is trained based on the generator model achieving a threshold level of laser speckle reduction on a set of validation images included in the validation data.

In some implementations, based on training the laser speckle reduction model, image processing platform 110 may store the laser speckle reduction model for use with imaging device 130. In some implementations, based on training the laser speckle reduction model, image processing platform 110 may provide the laser speckle reduction model for use with other imaging devices 130.

As shown in FIG. 1B, and by reference number 172, image processing platform 110 may cause imaging device 130 to capture an image, such as during an endoscopy procedure or another type of medical procedure. For example, client device 120 may receive operator input associated with triggering image capture, and client device 120 may provide an indication of the operator input to image processing platform 110. In this case, based on the indication of the operator input, image processing platform 110 may provide control data to cause imaging device 130 to capture an image. Additionally, or alternatively, image processing platform 110 may automatically cause imaging device 130 to perform imaging without operator input.

As further shown in FIG. 1B, and by reference number 174, image processing platform 110 may receive imaging data from imaging device 130 after imaging device 130 is caused to capture an image. For example, image processing platform 110 may receive an image illuminated under coherent energy illumination, incoherent energy illumination, and/or the like. In some implementations, image processing platform 110 may receive a static image. In some implementations, image processing platform 110 may receive a video. In some implementations, image processing platform 110 may receive multiple images, such as pairs of coherent energy illuminated images and incoherent energy illuminated images, multiple coherent energy illuminated images associated with different bandwidths of light, and/or the like. In some implementations, image processing platform 110 may receive imaging data without requesting imaging data, such as based on an operator interacting with imaging device 130 to cause imaging device 130 to perform imaging.

In some implementations, image processing platform 110 may use the laser speckle reduction model to reduce laser speckle in the imaging. For example, based on receiving, from imaging device 130, imaging data including a coherent energy illuminated image, image processing platform 110 may use the generator model of the laser speckle reduction model to generate a laser speckle-reduced image, thereby enabling improved identification and/or diagnostics based on the laser speckle-reduced image, relative to using the coherent energy illuminated image that includes laser speckle. In some implementations, image processing platform 110 may reduce noise (e.g., laser speckle) in the laser speckle-reduced image by greater than 2.5 decibels (dB), 2.9 dB, 3.0 dB, 3.5 dB, 5 dB, 6 dB, and/or the like. In some implementations, when other laser speckle reduction techniques are used in combination with the laser speckle reduction model, image processing platform 110 may generate an image with noise reduced by greater than 9 dB relative to a non-laser speckle reduced image. In some implementations, image processing platform 110 may provide the laser speckle-reduced image to client device 120 for output, as shown by reference number 176, thereby enabling the operator to perform a diagnosis, to guide a medical procedure, and/or the like. Additionally, or alternatively, image processing platform 110 may generate and provide an illumination corrected image (e.g., altered version of an image captured under dim illumination or excessively bright illumination) or another type of enhanced image, as described herein.

In some implementations, image processing platform 110 may perform automated image analysis based on the laser speckle-reduced image. For example, using a diagnostics model, image processing platform 110 may analyze the laser speckle-reduced image to identify one or more characteristics of the laser speckle-reduced image, such as a lesion, a mass, an object, and/or the like. In this case, image processing platform 110 may provide information identifying a result of the automated image analysis for display, such as a diagnosis, an augmented image (e.g., highlighting a detected characteristic), and/or the like. In some implementations, image processing platform 110 may identify a diagnosis based on a location of laser speckle. For example, laser speckle may be concentrated at a lesion or mass of a tissue, and based on identifying laser speckle in the coherent energy illuminated image to reduce laser speckle, image processing platform 110 may identify a location of the laser speckle in the coherent energy illuminated image as having a lesion or a mass.

In this way, image processing platform 110 uses the cGANs technique (e.g., by using a generator model and a discriminator model) to reduce laser speckle, thereby enabling use of coherent energy illumination for image capture and thereby improving medical diagnostics and/or other fields.

As indicated above, FIGS. 1A and 1B are provided merely as an example. Other examples may differ from what was described with regard to FIGS. 1A and 1B.

Figure 2A:
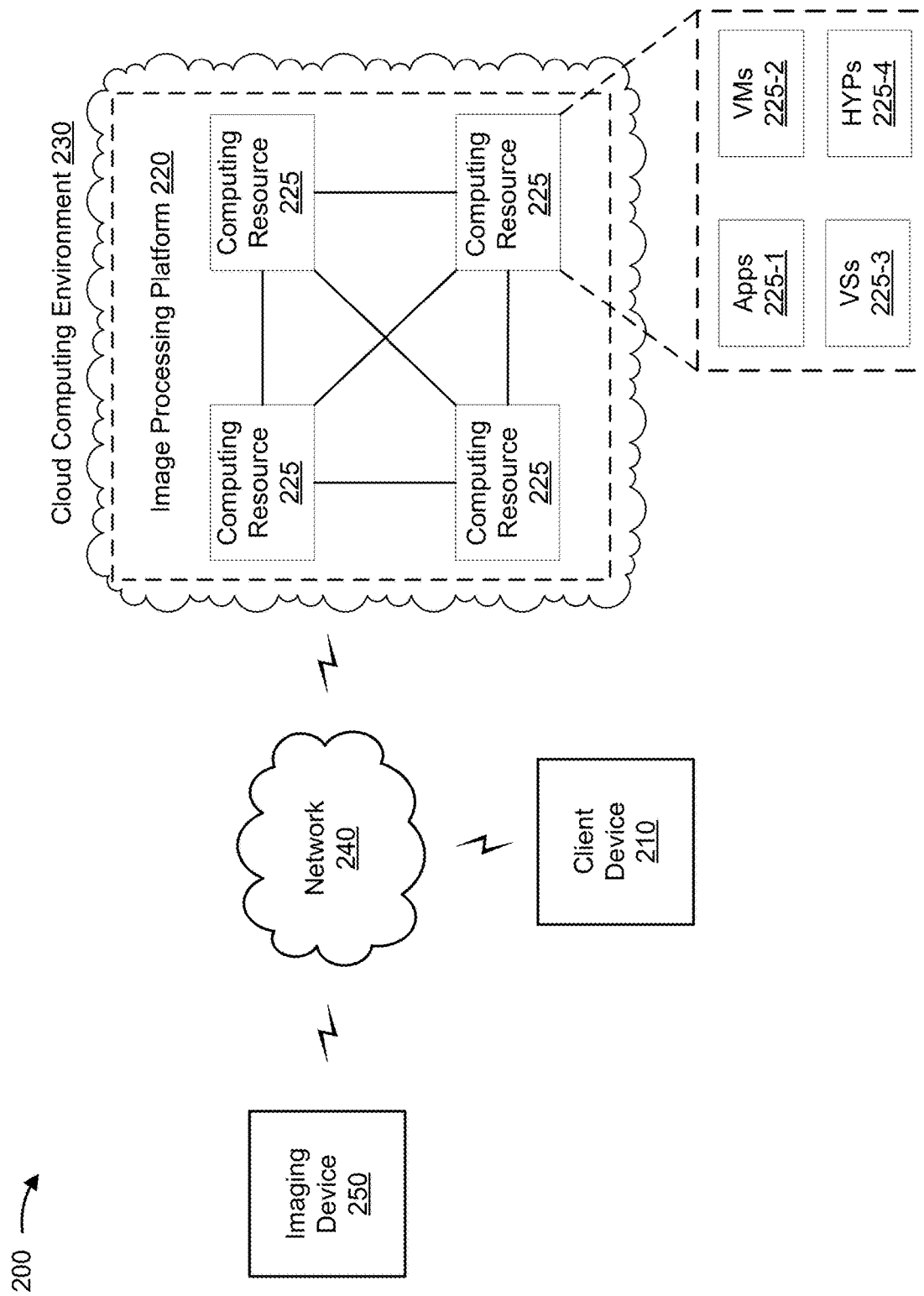
FIGS. 2A and 2B are diagrams of an example environment in which systems and/or methods described herein may be implemented.
Figure 2B:
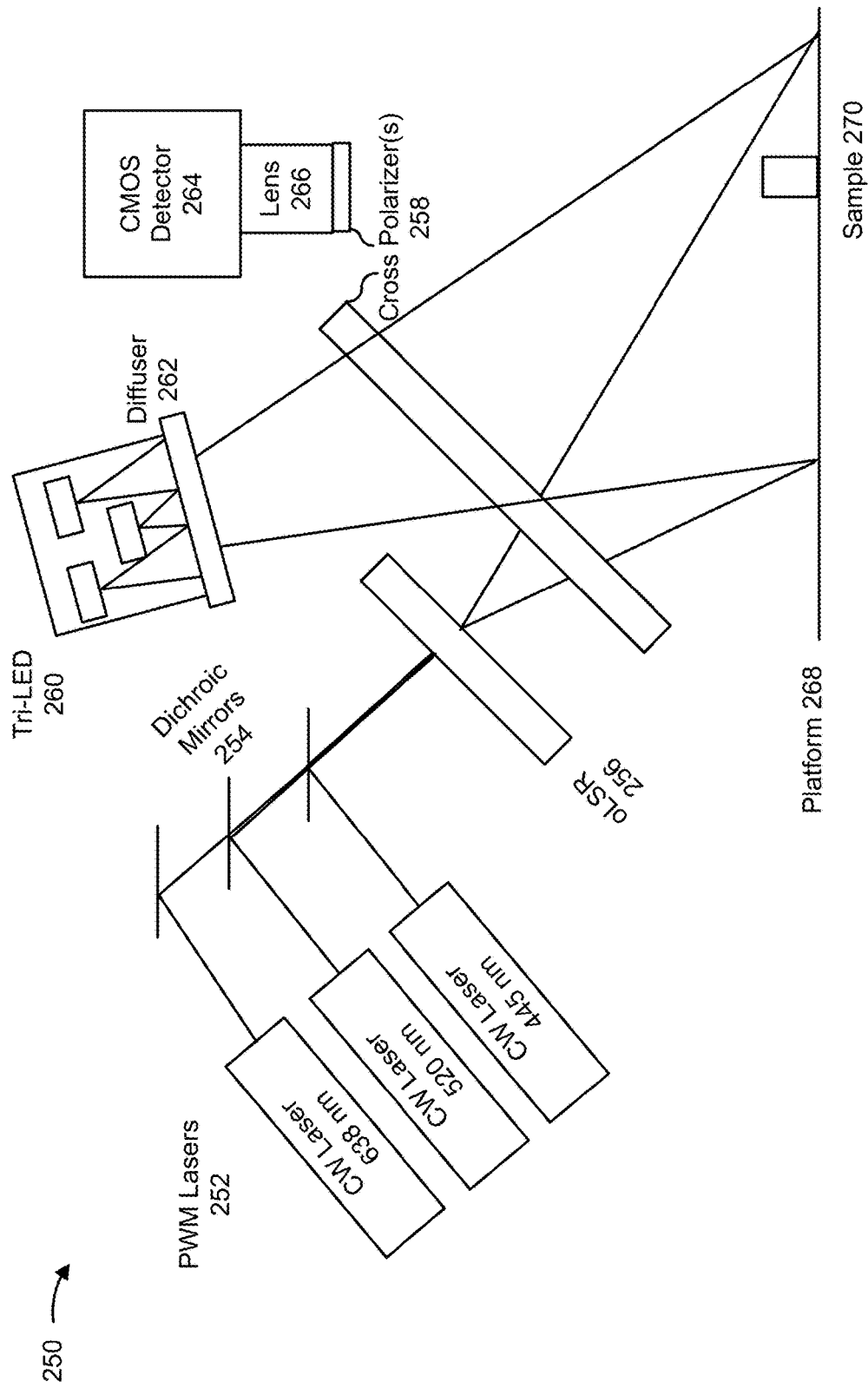

FIGS. 2A and 2B are diagrams of an example environment 200 in which systems and/or methods described herein may be implemented. As shown in FIG. 2A, environment 200 may include client device 210, an image processing platform 220, a computing resource 225, a cloud computing environment 230, a network 240, and an imaging device 250. Devices of environment 200 may interconnect via wired connections, wireless connections, or a combination of wired and wireless connections.

Client device 210 includes one or more devices capable of receiving, generating, storing, processing, and/or providing information, such as information described herein. For example, client device 210 may include a computer (e.g., a desktop computer, a laptop computer, a tablet computer, a handheld computer), mobile phone (e.g., a smart phone), a wearable communication device (e.g., a smart wristwatch, a pair of smart eyeglasses, and/or the like), a diagnostic device, and/or a similar type of device. In some implementations, client device 210 may include a display device to display a laser speckle-reduced image, an augmented image, and/or the like. In some implementations, client device 210 may include a communication interface that allows client device 210 to receive information from and/or transmit information to other devices in environment 200.

Image processing platform 220 includes one or more computing resources assigned to process an image to perform laser speckle reduction on a coherent energy illuminated image. For example, image processing platform 220 may be a platform implemented by cloud computing environment 230 that may generate a laser speckle-reduced image, perform a diagnosis based on the laser speckle-reduced image, and/or the like. In some implementations, image processing platform 220 is implemented by computing resources 225 of cloud computing environment 230. In some implementations, image processing platform 220 may include an imaging processing setup that derives one or more images from the input image, such as a flow map, a suspicious lesion mask, a depth map, and/or a narrow-band image. In some implementations, derived images may be used for computer-aided detection and/or diagnosis.

In some implementations, image processing platform 220 may be designed to be modular such that certain software components may be swapped in or out depending on a particular need. As such, image processing platform 220 may be easily and/or quickly reconfigured for different uses. In some implementations, image processing platform 220 may receive information from and/or transmit information to one or more imaging devices 250 and/or client devices 210. Notably, while implementations described herein describe image processing platform 220 as being hosted in cloud computing environment 230, in some implementations, image processing platform 220 may not be cloud-based (i.e., may be implemented outside of a cloud computing environment) or may be partially cloud-based.

Cloud computing environment 230 includes an environment that delivers computing as a service, whereby shared resources, services, etc. may be provided to process an image, such as to perform image processing to reduce laser speckle in an image. Cloud computing environment 230 may provide computation, software, data access, storage, and/or other services that do not require end-user knowledge of a physical location and configuration of a system and/or a device that delivers the services. As shown, cloud computing environment 230 may include image processing platform 220 and computing resource 225.

Computing resource 225 includes one or more personal computers, workstation computers, server devices, or another type of computation and/or communication device. In some implementations, computing resource 225 may host image processing platform 220. The cloud resources may include compute instances executing in computing resource 225, storage devices provided in computing resource 225, data transfer devices provided by computing resource 225, etc. In some implementations, computing resource 225 may communicate with other computing resources 225 via wired connections, wireless connections, or a combination of wired and wireless connections.

As further shown in FIG. 2, computing resource 225 may include a group of cloud resources, such as one or more applications ("APPs") 225-1, one or more virtual machines ("VMs") 225-2, virtualized storage ("VSs") 225-3, one or more hypervisors ("HYPs") 225-4, or the like.

Application 225-1 includes one or more software applications that may be provided to or accessed by client device 210 and/or imaging device 250. Application 225-1 may eliminate a need to install and execute the software applications on client device 210 and/or imaging device 250. For example, application 225-1 may include software associated with client device 210 and/or imaging device 250 and/or any other software capable of being provided via cloud computing environment 230. In some implementations, one application 225-1 may send/receive information to/from one or more other applications 225-1, via virtual machine 225-2.

Virtual machine 225-2 includes a software implementation of a machine (e.g., a computer) that executes programs like a physical machine. Virtual machine 225-2 may be either a system virtual machine or a process virtual machine, depending upon use and degree of correspondence to any real machine by virtual machine 225-2. A system virtual machine may provide a complete system platform that supports execution of a complete operating system. A process virtual machine may execute a single program, and may support a single process. In some implementations, virtual machine 225-2 may execute on behalf of a user (e.g., client device 210), and may manage infrastructure of cloud computing environment 230, such as data management, synchronization, or long-duration data transfers.

Virtualized storage 225-3 includes one or more storage systems and/or one or more devices that use virtualization techniques within the storage systems or devices of computing resource 225. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 225-4 provides hardware virtualization techniques that allow multiple operating systems (e.g., "guest operating systems") to execute concurrently on a host computer, such as computing resource 225. Hypervisor 225-4 may present a virtual operating platform to the guest operating systems, and may manage the execution of the guest operating systems. Multiple instances of a variety of operating systems may share virtualized hardware resources.

Network 240 includes one or more wired and/or wireless networks. For example, network 240 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

Imaging device 250 includes one or more devices capable of receiving, generating, storing, processing, and/or providing information associated with image capture. For example, imaging device 250 may include an image camera, an image sensor, a video camera, a microphone, a mobile phone (e.g., a smart phone, a radiotelephone, etc.), a laptop computer, a tablet computer, a handheld computer, a gaming device, a wearable communication device (e.g., a smart wristwatch, a pair of smart eyeglasses, etc.), or a similar type of device. In some implementations, imaging device 250 may transmit image data associated with an image to image processing platform 220. In some implementations, imaging device 250 may include a laser source to provide light in and to capture light in a particular bandwidth channel, such as a red bandwidth channel, a green bandwidth channel, a blue bandwidth channel, a near-infrared bandwidth channel, and/or the like. In some implementations, imaging device 250 may capture a coherent energy illuminated image and an incoherent energy illuminated image. In some implementations, imaging device 250 may include and/or be associated with one or more other components, such as a light source (e.g., a laser, a laser diode, and/or the like), a medical device (e.g., an endoscope), and/or the like. In some implementations, imaging device 250 may include a light guide to direct light from a light source of imaging device 250 to an object for imaging and/or to direct light from the object to a sensor to measure the light.

As shown in FIG. 2B, imaging device 250 may include a set of pulse-wave modulated (PWM) lasers 252, a set of dichroic mirrors 254, an optical laser speckle reducer (oLSR) 256, a set of cross polarizers 258, a tri-light emitting diode (tri-LED) 260, a diffuser 262, a complementary metal-oxide semi-conductor (CMOS) detector 264, a lens 266, and/or the like. For example, PWM lasers 252 may include multiple continuous wave lasers providing light at multiple wavelengths, such as a first PWM laser 252 providing light at 638 nanometers (nm), a second PWM laser 252 providing light at 520 nm, and a third PWM laser 252 providing light at 445 nm. In some implementations, PWM lasers 252 may provide multiple different channels of light, such as a red channel, a blue channel, a green channel, an infrared channel, a combination thereof, and/or the like.

In some implementations, PWM lasers 252 may be driven using different pulse-width modulation patterns. In some implementations, dichroic mirrors 254 may direct light from PWM lasers 252 toward oLSR 256 and a cross polarizer 258 to cause the light to be directed to platform 268 (e.g., a Teflon platform) and a sample 270 thereon. In some implementations, oLSR 256 may be toggled on and off to enable imaging of sample 270 with and/or without speckle (e.g., during training). In some implementations, during operation, oLSR 256 may be toggled off and/or removed from an optical path to enable illumination of sample 270 with speckled light, as described above.

In some implementations, tri-LED 260 may provide light at a half maximum of an illumination profile of the set of PWM lasers 252. In some implementations, CMOS detector 264 may perform imaging of the sample 270 (e.g., based on illumination by PWM lasers 252, tri-LED 260, and/or the like). In this case, such as during training, imaging device 250 may capture images illuminated using the set of PWM lasers 252 with oLSR 256 toggled off, images illuminated using the set of PWM lasers 252 with oLSR 256 toggled on, and images illuminated using tri-LED 260, thereby enabling acquisition of a training set that includes laser speckled images, speckle-reduced images, and non-speckled images for training a laser speckle reduction model.

The number and arrangement of devices and networks shown in FIGS. 2A-2B are provided as an example. In practice, there may be additional devices and/or networks, fewer devices and/or networks, different devices and/or networks, or differently arranged devices and/or networks than those shown in FIGS. 2A-2B. Furthermore, two or more devices shown in FIGS. 2A-2B may be implemented within a single device, or a single device shown in FIGS. 2A-2B may be implemented as multiple, distributed devices. Additionally, or alternatively, a set of devices (e.g., one or more devices) of environment 200 may perform one or more functions described as being performed by another set of devices of environment 200.

Figure 3:
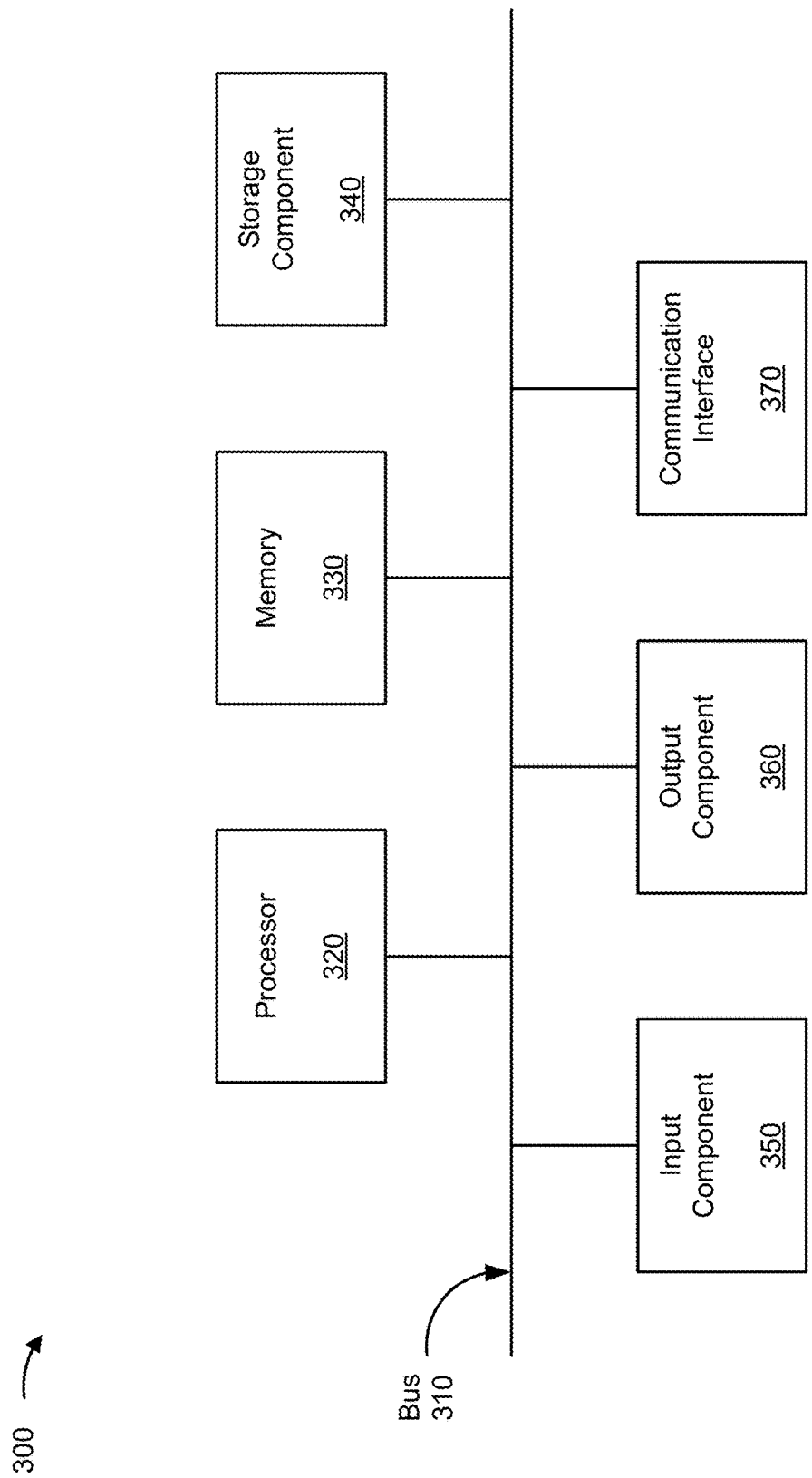
FIG. 3 is a diagram of example components of one or more devices of FIG. 2.

FIG. 3 is a diagram of example components of a device 300. Device 300 may correspond to or include client device 210, image processing platform 220, computing resource 225, and/or imaging device 250. In some implementations, client device 210, image processing platform 220, computing resource 225, and/or imaging device 250 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes based on to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
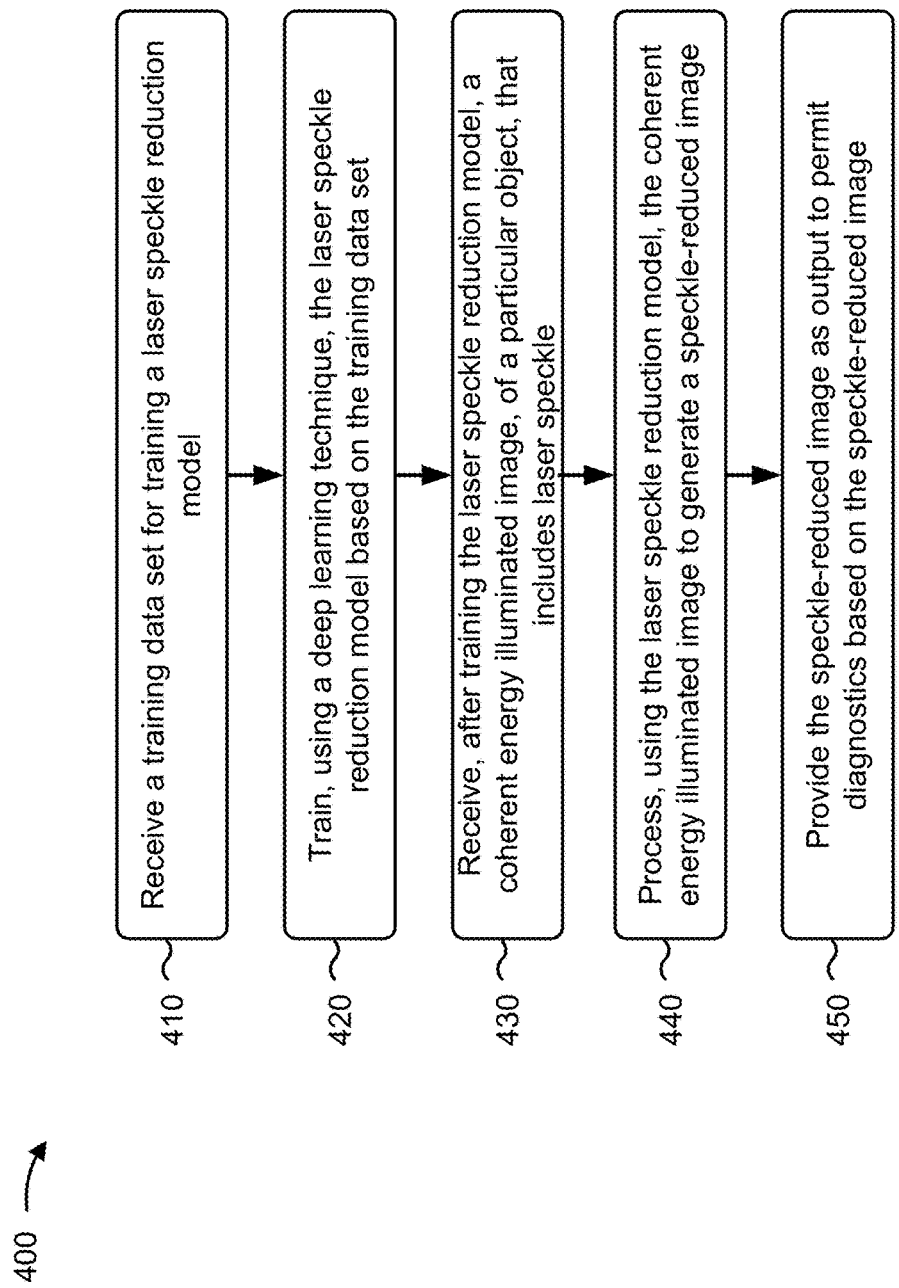
FIGS. 4-6 are flow charts of an example processes for laser speckle reduction of an image illuminated with coherent energy.

FIG. 4 is a flow chart of an example process 400 for laser speckle reduction for a coherent energy illuminated image. In some implementations, one or more process blocks of FIG. 4 may be performed by an image processing platform (e.g., image processing platform 220). In some implementations, one or more process blocks of FIG. 4 may be performed by another device or a group of devices separate from or including the image processing platform (e.g., image processing platform 220), such as a client device (e.g., client device 210), an imaging device (e.g., imaging device 250), and/or the like.

As shown in FIG. 4, process 400 may include receiving a training data set for training a laser speckle reduction model (block 410). For example, the image processing platform (e.g., using computing resource 225, bus 310, processor 320, memory 330, storage component 340, input component 350, output component 360, communication interface 370, and/or the like) may receive a training data set for training a laser speckle reduction model, as described in more detail above. In some implementations, the training data set includes a set of image pairs of training objects. In some implementations, an image pair, of the set of image pairs, includes a first image, of a training object of the training objects, that includes laser speckle and a second image, of the training object, that includes less laser speckle than the first image.

As further shown in FIG. 4, process 400 may include training, using a deep learning technique, the laser speckle reduction model based on the training data set (block 420). For example, the image processing platform (e.g., using computing resource 225, bus 310, processor 320, memory 330, storage component 340, input component 350, output component 360, communication interface 370, and/or the like) may train, using a deep learning technique, the laser speckle reduction model based on the training data set, as described in more detail above. In some implementations, the laser speckle reduction model comprises a generator model to generate a reduced laser speckle image and a discriminator model to train the generator model.

As further shown in FIG. 4, process 400 may include receiving, after training the laser speckle reduction model, a coherent energy illuminated image, of a particular object, that includes laser speckle (block 430). For example, the image processing platform (e.g., using computing resource 225, bus 310, processor 320, memory 330, storage component 340, input component 350, output component 360, communication interface 370, and/or the like) may receive, after training the laser speckle reduction model, a coherent energy illuminated image, of a particular object not included in the training objects, that includes laser speckle, as described in more detail above.

As further shown in FIG. 4, process 400 may include processing, using the laser speckle reduction model, the coherent energy illuminated image to generate a laser speckle-reduced image (block 440). For example, the image processing platform (e.g., using computing resource 225, bus 310, processor 320, memory 330, storage component 340, input component 350, output component 360, communication interface 370, and/or the like) may process, using the laser speckle reduction model, the coherent energy illuminated image to generate a laser speckle-reduced image, as described in more detail above.

As further shown in FIG. 4, process 400 may include providing the laser speckle-reduced image as output to permit diagnostics based on the laser speckle-reduced image (block 450). For example, the image processing platform (e.g., using computing resource 225, bus 310, processor 320, memory 330, storage component 340, input component 350, output component 360, communication interface 370, and/or the like) may provide the laser speckle-reduced image as output to permit diagnostics based on the laser speckle-reduced image, as described in more detail above.

Process 400 may include additional implementations, such as any single implementation or any combination of implementations described below and/or in connection with one or more other processes described elsewhere herein.

In a first implementation, the image processing platform may perform image processing on the laser speckle-reduced image to identify a characteristic of the laser speckle-reduced image, and may provide output associated with the characteristic of the laser speckle-reduced image. In a second implementation, alone or in combination with the first implementation, the particular object is a medical object and the characteristic is a diagnostic characteristic of the laser speckle-reduced image. In a third implementation, alone or in combination with one or more of the first and second implementations, the coherent energy illuminated image is received from an endoscopic imaging system.

In a fourth implementation, alone or in combination with one or more of the first through third implementations, the generator model is a trained neural network. In a fifth implementation, alone or in combination with one or more of the first through fourth implementations, the coherent energy illuminated image is altered using one or more additional laser speckle-reduction techniques before the processing of the coherent energy illuminated image. In a sixth implementation, alone or in combination with one or more of the first through fifth implementations, the image processing platform may segment the image pair into a set of image segment pairs, wherein an image segment pair, of the set of image segment pairs, includes a first image segment that includes laser speckle and a corresponding second image segment that does not include laser speckle, and may train the laser speckle reduction model using the set of image segment pairs.

In a seventh implementation, alone or in combination with one or more of the first through sixth implementations, the generator model and the discriminator model are conditional generative adversarial networks. In an eighth implementation, alone or in combination with one or more of the first through seventh implementations, the coherent energy illuminated image is illuminated using a plurality of channels of illumination, and the plurality of channels includes at least one of: a red channel, a green channel, a blue channel, or a near-infrared channel. In a ninth implementation, alone or in combination with one or more of the first through eighth implementations, the image processing platform may process the coherent energy illuminated image in connection with an incoherent energy illuminated image, and may provide output connected with the laser speckle-reduced image and the incoherent energy illuminated image.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
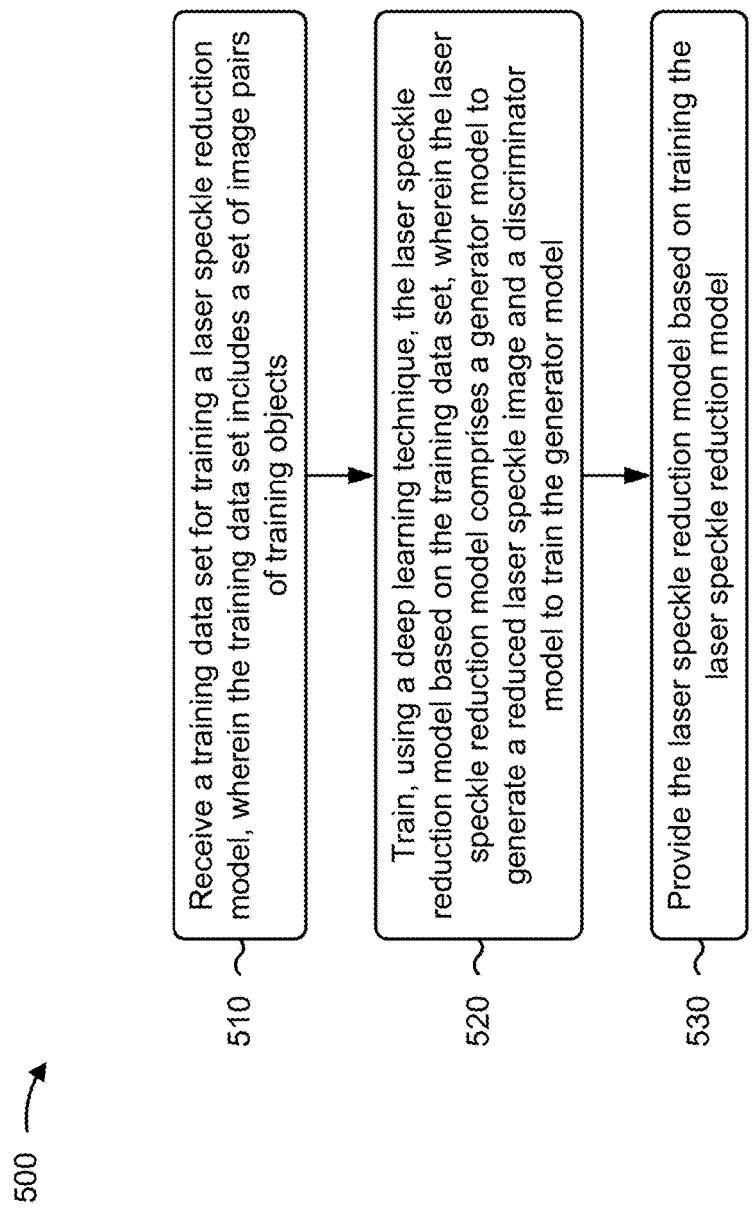

FIG. 5 is a flow chart of an example process 500 for deep learning based laser speckle reduction for imaging. In some implementations, one or more process blocks of FIG. 5 may be performed by an image processing platform (e.g., image processing platform 220). In some implementations, one or more process blocks of FIG. 5 may be performed by another device or a group of devices separate from or including the image processing platform, such as a client device (e.g., client device 210), an imaging device (e.g., imaging device 250), and/or the like.

As shown in FIG. 5, process 500 may include receiving a training data set for training a laser speckle reduction model, wherein the training data set includes a set of image pairs of training objects (block 510). For example, the image processing platform (e.g., using processor 320, memory 330, storage component 340, input component 350, output component 360, communication interface 370 and/or the like) may receive a training data set for training a laser speckle reduction model, as described above. In some implementations, the training data set includes a set of image pairs of training objects.

As further shown in FIG. 5, process 500 may include training, using a deep learning technique, the laser speckle reduction model based on the training data set, wherein the laser speckle reduction model comprises a generator model to generate a reduced laser speckle image and a discriminator model to train the generator model (block 520). For example, the image processing platform (e.g., using processor 320, memory 330, storage component 340, input component 350, output component 360, communication interface 370 and/or the like) may train, using a deep learning technique, the laser speckle reduction model based on the training data set, as described above. In some implementations, the laser speckle reduction model comprises a generator model to generate a reduced laser speckle image and a discriminator model to train the generator model.

As further shown in FIG. 5, process 500 may include providing the laser speckle reduction model based on training the laser speckle reduction model (block 530). For example, the image processing platform (e.g., using processor 320, memory 330, storage component 340, input component 350, output component 360, communication interface 370 and/or the like) may provide the laser speckle reduction model based on training the laser speckle reduction model, as described above.

Process 500 may include additional implementations, such as any single implementation or any combination of implementations described below and/or in connection with one or more other processes described elsewhere herein.

In a first implementation, process 500 includes receiving, after training the laser speckle reduction model, a coherent energy illuminated image, of a particular object not included in the training object, that includes laser speckle; processing, using the laser speckle reduction model, the coherent energy illuminated image to generate a laser speckle-reduced image; providing the laser speckle-reduced image as output to permit diagnostics based on the laser speckle-reduced image; performing image processing on the laser speckle-reduced image to identify a characteristic of the laser speckle-reduced image; and providing output associated with the characteristic of the laser speckle-reduced image.

In a second implementation, alone or in combination with the first implementation, the laser speckle-reduced image is associated with a greater than 3 decibel (dB) reduction in noise relative to the coherent energy illuminated image.

In a third implementation, alone or in combination with one or more of the first and second implementations, the deep learning technique is a conditional generative adversarial networks (cGANS) neural network technique.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
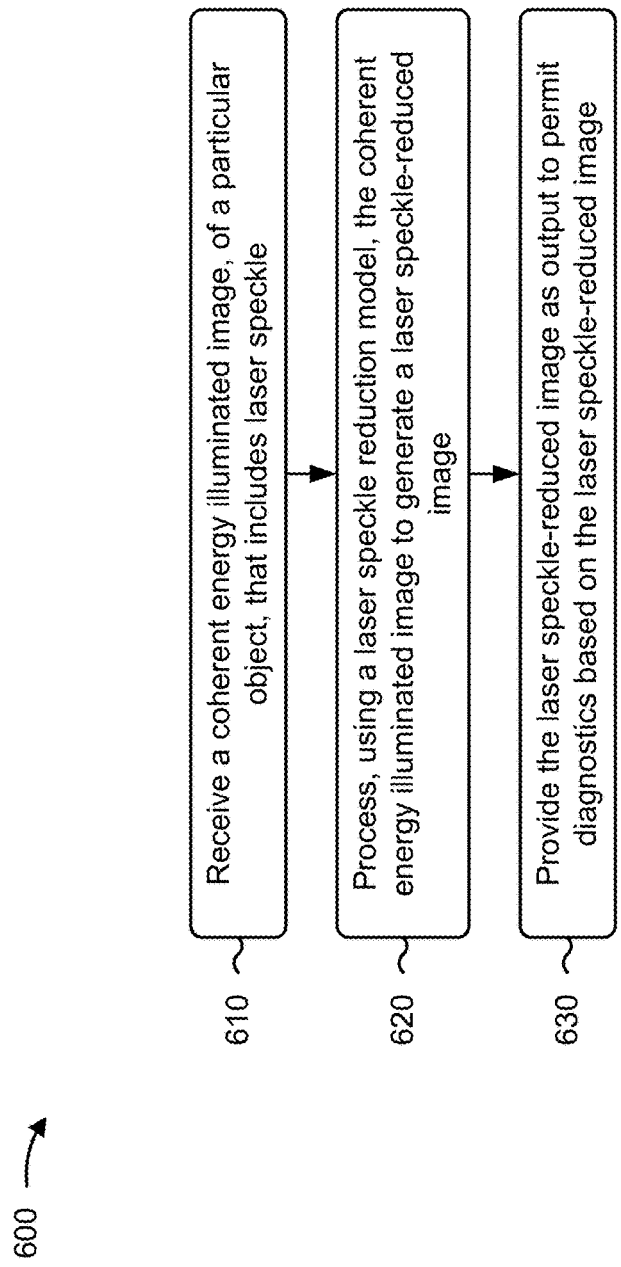

FIG. 6 is a flow chart of an example process 600 for deep learning based laser speckle reduction for imaging. In some implementations, one or more process blocks of FIG. 6 may be performed by an image processing platform (e.g., image processing platform 220). In some implementations, one or more process blocks of FIG. 6 may be performed by another device or a group of devices separate from or including the image processing platform, such as a client device (e.g., client device 210), an imaging device (e.g., imaging device 250), and/or the like.

As shown in FIG. 6, process 600 may include receiving a coherent energy illuminated image, of a particular object, that includes laser speckle (block 610). For example, the image processing platform (e.g., using processor 320, memory 330, storage component 340, input component 350, output component 360, communication interface 370 and/or the like) may receive a coherent energy illuminated image, of a particular object, that includes laser speckle, as described above.

As further shown in FIG. 6, process 600 may include processing, using a laser speckle reduction model, the coherent energy illuminated image to generate a laser speckle-reduced image (block 620). For example, the image processing platform (e.g., using processor 320, memory 330, storage component 340, input component 350, output component 360, communication interface 370 and/or the like) may process, using a laser speckle reduction model, the coherent energy illuminated image to generate a laser speckle-reduced image, as described above.

As further shown in FIG. 6, process 600 may include providing the laser speckle-reduced image as output to permit diagnostics based on the laser speckle-reduced image (block 630). For example, the image processing platform (e.g., using processor 320, memory 330, storage component 340, input component 350, output component 360, communication interface 370 and/or the like) may provide the laser speckle-reduced image as output to permit diagnostics based on the laser speckle-reduced image, as described above.

Process 600 may include additional implementations, such as any single implementation or any combination of implementations described below and/or in connection with one or more other processes described elsewhere herein.

In a first implementation, the laser speckle-reduced image is associated with a greater than 5 decibel (dB) reduction in noise relative to the coherent energy illuminated image.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise form disclosed. Modifications and variations may be made possible in light of the above disclosure or may be acquired from practice of the implementations.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, or the like.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A device, comprising:
one or more memories; and
one or more processors, coupled to the one or more memories, to:
receive data for training a laser speckle reduction model,
wherein the data includes a set of image pairs of one or more training objects, and
wherein an image pair, of the set of image pairs, includes a first image and a second image that includes less laser speckle than the first image;
train the laser speckle reduction model based on the data;
determine that the laser speckle reduction model is trained based on achieving a threshold level of laser speckle reduction on a set of validation images;
receive, after training the laser speckle reduction model, a coherent energy illuminated image, of a particular object not included in the one or more training objects, that includes laser speckle;
process, based on the laser speckle reduction model, the coherent energy illuminated image and an incoherent energy illuminated image, to generate a laser speckle-reduced image; and
provide an output associated with the laser speckle-reduced image.

2. The device of claim 1, wherein the one or more processors are further to:
process the laser speckle-reduced image to identify a characteristic associated with the laser speckle-reduced image; and
provide output associated with the characteristic.

3. The device of claim 2, wherein the characteristic is a diagnostic characteristic.

4. The device of claim 1, wherein the coherent energy illuminated image is received from a medical imaging system.

5. The device of claim 1, wherein the one or more processors are further to:
process the laser speckle-reduced image to identify a diagnosis based on a location of laser speckle.

6. The device of claim 1, wherein the one or more processors are further to:
generate an augmented image based on the laser speckle-reduced image.

7. A non-transitory computer-readable medium storing a set of instructions, the set of instructions comprising:
one or more instructions that, when executed by one or more processors of a device, cause the device to:
receive data for training a laser speckle reduction model,
wherein the data includes a set of image pairs of one or more training objects, and
wherein an image pair, of the set of image pairs, includes a first image and a second image that includes less laser speckle than the first image;
train the laser speckle reduction model based on the data;
determine that the laser speckle reduction model is trained based on achieving a threshold level of laser speckle reduction on a set of validation images;
receive, after training the laser speckle reduction model, a coherent energy illuminated image, of a particular object not included in the one or more training objects, that includes laser speckle;
process, based on the laser speckle reduction model, the coherent energy illuminated image and an incoherent energy illuminated image, to generate a laser speckle-reduced image; and
provide an output associated with the laser speckle-reduced image.

8. The non-transitory computer-readable medium of claim 7, wherein the one or more instructions further cause the device to:
process the laser speckle-reduced image to identify a characteristic associated with the laser speckle-reduced image; and
provide output associated with the characteristic.

9. The non-transitory computer-readable medium of claim 8, wherein the characteristic is associated with a diagnostic characteristic.

10. The non-transitory computer-readable medium of claim 7, wherein the coherent energy illuminated image is received from a medical imaging system.

11. The non-transitory computer-readable medium of claim 7, wherein the one or more instructions further cause the device to:
process the laser speckle-reduced image to identify a diagnosis based on a location of laser speckle.

12. The non-transitory computer-readable medium of claim 7, wherein the one or more instructions further cause the device to:
generate an augmented image based on the laser speckle-reduced image.

13. A method, comprising:
receiving, by a device, data for training a laser speckle reduction model,
wherein the data includes a set of image pairs of one or more training objects, and
wherein an image pair, of the set of image pairs, includes a first image and a second image that includes less laser speckle than the first image;
training, by the device, the laser speckle reduction model based on the data;
determining, by the device, that the laser speckle reduction model is trained based on achieving a threshold level of laser speckle reduction on a set of validation images;
receiving, by the device and after training the laser speckle reduction model, a coherent energy illuminated image, of a particular object not included in the one or more training objects, that includes laser speckle;

processing, by the device and based on the laser speckle reduction model, the coherent energy illuminated image, to generate a laser speckle-reduced image; and providing, by the device, an output associated with the laser speckle-reduced image and an incoherent energy illuminated image.

14. The method of claim 13, further comprising:

processing the laser speckle-reduced image to identify a characteristic associated with the laser speckle-reduced image; and providing output associated with the characteristic.

15. The method of claim 14, wherein the characteristic is a diagnostic characteristic.

16. The method of claim 13, wherein the coherent energy illuminated image is received from a medical imaging system.

17. The method of claim 13, further comprising:

processing the laser speckle-reduced image to identify a diagnosis based on a location of laser speckle.

18. The device of claim 1, wherein the coherent energy illuminated image is received from an endoscopic imaging system.

19. The non-transitory computer-readable medium of claim 7, wherein the coherent energy illuminated image is received from an endoscopic imaging system.

20. The method of claim 13, wherein the coherent energy illuminated image is received from an endoscopic imaging system.

* * * * *